United States Patent
Anraku et al.

(10) Patent No.: US 10,677,778 B2
(45) Date of Patent: Jun. 9, 2020

(54) SERUM- OR PLASMA-SEPARATING COMPOSITION, BLOOD-TEST CONTAINER, AND METHOD OF STABILIZING SERUM- OR PLASMA-SEPARATING COMPOSITION

(71) Applicant: SEKISUI MEDICAL CO., LTD., Tokyo (JP)

(72) Inventors: Hideo Anraku, Yamaguchi (JP); Ryusuke Okamoto, Yamaguchi (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 258 days.

(21) Appl. No.: 15/576,689

(22) PCT Filed: Jun. 9, 2016

(86) PCT No.: PCT/JP2016/067210
§ 371 (c)(1),
(2) Date: Nov. 22, 2017

(87) PCT Pub. No.: WO2016/199851
PCT Pub. Date: Dec. 15, 2016

(65) Prior Publication Data
US 2018/0136192 A1     May 17, 2018

(30) Foreign Application Priority Data
Jun. 10, 2015 (JP) ................................ 2015-117449

(51) Int. Cl.
| | | |
|---|---|---|
| G01N 33/49 | (2006.01) | |
| C08L 57/02 | (2006.01) | |
| B01L 3/00 | (2006.01) | |
| C08L 45/00 | (2006.01) | |
| C08L 65/00 | (2006.01) | |

(52) U.S. Cl.
CPC ........ *G01N 33/491* (2013.01); *B01L 3/50215* (2013.01); *C08L 45/00* (2013.01); *C08L 57/02* (2013.01); *B01L 3/5082* (2013.01); *C08L 65/00* (2013.01); *C08L 2205/03* (2013.01); *C08L 2207/04* (2013.01)

(58) Field of Classification Search
CPC .. H04L 5/0032; H04L 5/0057; H04W 72/085; H04W 76/15; H04W 24/08; H04W 24/10; H04W 92/20
See application file for complete search history.

(56) References Cited

U.S. PATENT DOCUMENTS

| | | | |
|---|---|---|---|
| 4,049,692 A | 9/1977 | Zine, Jr. | |
| 4,083,784 A | 4/1978 | Zine, Jr. | |
| 4,235,725 A | 11/1980 | Semersky | |
| 4,994,393 A * | 2/1991 | Pradhan | ............... G01N 33/491 436/8 |
| 5,776,357 A | 7/1998 | Okamoto et al. | |
| 2004/0129631 A1 * | 7/2004 | Anraku | ............... B01L 3/50215 210/500.1 |
| 2010/0155343 A1 | 6/2010 | Battles et al. | |
| 2012/0070350 A1 | 3/2012 | Anraku et al. | |
| 2014/0238930 A1 | 8/2014 | Newby et al. | |
| 2016/0216178 A1 | 7/2016 | Newby et al. | |
| 2016/0216179 A1 | 7/2016 | Newby et al. | |

FOREIGN PATENT DOCUMENTS

| | | | | |
|---|---|---|---|---|
| CN | 1165558 A | 11/1997 | | |
| CN | 1533503 A | 9/2004 | | |
| CN | 102149473 A | 8/2011 | | |
| CN | 102309870 A | 1/2012 | | |
| CN | 102690387 A | 9/2012 | | |
| CN | 102741690 A | 10/2012 | | |
| CN | 102764133 A | 11/2012 | | |
| CN | 102872616 A * | 1/2013 | ........... | G01N 33/491 |
| CN | 102872616 A | 11/2013 | | |
| EP | 1 106 251 B1 | 11/2005 | | |
| EP | 2 410 329 A1 | 1/2012 | | |
| JP | 59-11863 B2 | 3/1984 | | |
| JP | 10-10122 A | 1/1998 | | |
| JP | 2001-165928 A | 6/2001 | | |
| JP | 2002-365282 A | 12/2002 | | |
| JP | 2013-61283 A | 4/2013 | | |
| WO | WO-2011/105151 A1 | 9/2011 | | |

OTHER PUBLICATIONS

Supplementary European Search Report for the Application No. EP 16 807 557.0 dated Feb. 13, 2019.
The First Office Action for the Application No. 201680033584.X from The State Intellectual Property Office of the People's Republic of China dated Jan. 29, 2019.
Written Opinion of the International Searching Authority (PCT/ISA/237) for Application No. PCT/JP2016/067210 dated Aug. 16, 2016 (English Translation mailed Dec. 21, 2017).

(Continued)

*Primary Examiner* — Dennis White
(74) *Attorney, Agent, or Firm* — Cheng Law Group, PLLC

(57) ABSTRACT

There is provided a serum- or plasma-separating composition less likely to cause separation between a liquid organic compound and a thixotropy imparting component and capable of maintaining a homogeneous blended state for a prolonged period. The serum- or plasma-separating composition comprises a liquid organic compound, a thixotropy imparting component, and a thermoplastic elastomer.

10 Claims, No Drawings

(56) References Cited

OTHER PUBLICATIONS

International Search Report for the Application No. PCT/JP2016/067210 dated Aug. 16, 2016.
Written Opinion of the International Searching Authority (PCT/ISA/237) for Application No. PCT/JP2016/067210 dated Aug. 16, 2016.
The Third Office Action for the Application No. 201680033584.X from The State Intellectual Property Office of the People's Republic of China dated Dec. 30, 2019.

* cited by examiner

SERUM- OR PLASMA-SEPARATING COMPOSITION, BLOOD-TEST CONTAINER, AND METHOD OF STABILIZING SERUM- OR PLASMA-SEPARATING COMPOSITION

TECHNICAL FIELD

The present invention relates to a serum- or plasma-separating composition used for separating serum or plasma from blood, more specifically for separating serum or plasma from blood using a difference in the specific gravities between blood components, a blood-test container containing the serum- or plasma-separating composition therein, and a method of stabilizing the serum- or plasma-separating composition.

BACKGROUND ART

In the clinical laboratory field, techniques for separating serum or plasma from blood by centrifugation using a difference in the specific gravities between blood components are widely used. In order to prevent the separated components from mixing again, various serum- or plasma-separating compositions having a specific gravity adjusted to 1.03 to 1.08 have been conventionally suggested.

As the above-described serum- or plasma-separating composition, thixotropic compositions have been widely used, from the viewpoint of stability during transport and storage, and also from the viewpoint of enabling stable maintenance of a separated state even after centrifugation. Use of a thixotropic composition can simplify blood separation, irrespective of skills of the user.

The following Patent Literature 1 discloses a serum- or plasma-separating composition comprising a liquid organic compound component, and an inorganic powder dispersed in the liquid organic compound for the purpose of adjusting the specific gravity and imparting a thixotropic-property. Patent Literatures 1 and 2 disclose serum- or plasma-separating compositions comprising various organic compounds such as a polyoxyethylene polyoxypropylene block copolymer or a silicone-based surfactant as a thixotropic-property enhancer.

CITATION LIST

Patent Literature

Patent Literature 1: Japanese Patent Laid-Open No. 10-10122
Patent Literature 2: Japanese Patent Laid-Open No. 59-11863

SUMMARY OF INVENTION

Technical Problem

The thixotropic-property imparting agent and the thixotropic-property enhancer disclosed in Patent Literatures 1 and 2 are intended to obtain a thixotropic-property by forming a hydrogen-bonding-based network in a liquid organic compound.

Impartation of thixotropic-property by use of hydrogen bonding, which can be achieved with easily-available materials, is widely used. The materials involved in such a hydrogen-bonding-based network, however, aggregate over time due to their own strong aggregation property based on the hydrogen bonding. Consequently, localization of the thixotropic-property imparting component is caused. This may lead to a state called a phase separation, where island domains, in which the thixotropic-property imparting component exists at relatively high concentrations, and a sea domain, in which the thixotropic-property imparting component sparsely exists, are separated.

Therefore, the liquid organic compound is liberated from the serum- or plasma-separating compositions disclosed in Patent Literatures 1 and 2 due to the phase separation, and may spread along and wet the inner surface of a blood collection tube. Tearing of the components of the serum- or plasma-separating compositions is caused to generate oil drops or oil film. As a result of this, measurement results and measurement devices may be influenced.

An object of the present invention is to provide a serum- or plasma-separating composition less likely to cause separation between a liquid organic compound and a thixotropic-property imparting component and capable of maintaining a homogeneously blended state for a prolonged period, a blood-test container containing the serum- or plasma-separating composition therein, and a method of stabilizing the serum- or plasma-separating composition.

Solution to Problem

The present inventors have intensively studied to find that a thermoplastic elastomer is additionally blended to a composition containing a liquid organic compound and a thixotropic-property imparting component to thereby obtain a serum- or plasma-separating composition which is less likely to cause separation between these constituents and can maintain a homogeneously blended state for a prolonged period, thus having completed the present invention.

The serum- or plasma-separating composition according to the present invention comprises a liquid organic compound, a thixotropic-property imparting component, and a thermoplastic elastomer.

In a specific aspect of the serum- or plasma-separating composition according to the present invention, the liquid organic compound comprises a liquid resin.

In another specific aspect of the serum- or plasma-separating composition according to the present invention, the thermoplastic elastomer is at least one selected from the group consisting of styrene-based thermoplastic elastomers, urethane-based thermoplastic elastomers, ester-based thermoplastic elastomers, amide-based thermoplastic elastomers, acryl-based thermoplastic elastomers, and olefin-based thermoplastic elastomers.

In another specific aspect of the serum- or plasma-separating composition according to the present invention, the thermoplastic elastomer is a styrene-based thermoplastic elastomer.

In still another specific aspect of the serum- or plasma-separating composition according to the present invention, the content of the thermoplastic elastomer is 0.5 to 50% by weight.

In still another specific aspect of the serum- or plasma-separating composition according to the present invention, the liquid organic compound is a mixture of at least one of a petroleum resin and a dicyclopentadiene resin with a benzene polycarboxylic acid alkyl ester.

In still another specific aspect of the serum- or plasma-separating composition according to the present invention, an inorganic fine powder is contained as the thixotropic-property imparting component.

In still another specific aspect of the serum- or plasma-separating composition according to the present invention, the inorganic fine powder is at least one of hydrophilic silica and hydrophobic silica.

In still another specific aspect of the serum- or plasma-separating composition according to the present invention, the serum- or plasma-separating composition further contains an organic gelling agent.

The blood-test container according to the present invention contains the serum- or plasma-separating composition constituted according to the present invention therein.

In the method of stabilizing a serum- or plasma-separating composition according to the present invention, the serum- or plasma-separating composition comprising a liquid organic compound and a thixotropic-property imparting component is allowed to additionally contain a thermoplastic elastomer.

Advantageous Effects of Invention

The serum- or plasma-separating composition provided by the present invention, in which the thermoplastic elastomer is blended in addition to the liquid organic compound and the thixotropic-property imparting component, is less likely to cause separation between the liquid organic compound and the thixotropic-property imparting component and can maintain the homogeneity as a blend over a prolonged period, even when exposed to a high temperature of 50 to 60° C.

The blood-test container according to the present invention, which contains the serum- or plasma-separating composition provided according to the aspects described above, is unlikely to cause flowing due to phase separation of the serum- or plasma-separating composition during transport or storage of the blood-test container.

Thus, contamination of other agents such as an anticoagulant agent, a blood coagulation accelerator, or a glycolytic inhibitor contained in the above-described blood-test container can be prevented. Additionally, the partition wall composed of the serum- or plasma-separating composition is difficult to collapse after centrifugation, and thus the serum or plasma and the blood cell constituents, once separated, would not be mixed again. Furthermore, oil drops or oil film are difficult to liberate from the serum- or plasma-separating composition, and test devices would not be contaminated. Accordingly, each component in serum or plasma can be measured highly precisely.

DESCRIPTION OF EMBODIMENT

The details of the present invention will be described hereinafter.

(Serum- or Plasma-Separating Composition)

The serum- or plasma-separating composition according to the present invention comprises a liquid organic compound, a thixotropic-property imparting component, and a thermoplastic elastomer. Thus, the serum- or plasma-separating composition of the present invention is less likely to cause separation between the liquid organic compound and the thixotropic-property imparting component and can maintain a homogeneously blended state for a prolonged period.

Hereinafter each of the materials constituting the serum- or plasma-separating composition of the present invention will be described.

Liquid Organic Compound;

The serum- or plasma-separating composition of the present invention contains a liquid organic compound.

The liquid organic compound in the serum- or plasma-separating composition of the present invention comprises a resin that becomes a liquid state at −10° C. or more, in consideration of the temperature range where a blood specimen freezes. No particular limitation is place on the liquid organic compound provided that the composition has fluidity required for developing partition-wall formability as well as satisfies a required specific gravity.

A state of having the required fluidity herein means that the viscosity at 25° C. (shear rate=1 sec$^{-1}$) in a BROOKFIELD-type rotational viscometer equipped with a cone-plate type rotor is 500 Pa·s or less. A state of satisfying the specific gravity herein means that the ratio between the density of the liquid organic compound at 25° C. and that of water at 4° C. is from 0.9 to 1.1.

As such a liquid organic compound, liquid resin is preferable. No particular limitation is placed on the liquid resin that can be used in the present invention, and examples thereof include any known liquid resin, such as silicone resins, α-olefin-fumaric acid ester copolymer resins, acrylic resins, polyester resins, copolymer resins of sebacic acid with 2,2-dimethyl-1,3-propanediol and 1,2-propanediol, polyether-polyurethane resins, and polyether-polyester resins.

As the liquid organic compound, liquid mixtures of a poly-α-pinene polymer and a chlorinated hydrocarbon, liquid mixtures of chlorinated polybutene and a epoxidized animal or vegetable oil or the like, liquid mixtures of trifluoroethylene chloride or a benzene polycarboxylic acid alkyl ester derivative or the like and a polyoxyalkylene glycol or the like, or liquid mixtures that are in the liquid form at −10° C. or more and are composed of a liquid/liquid or solid/liquid combination of a petroleum resin or a dicyclopentadiene resin or the like and a benzene polycarboxylic acid alkyl ester derivative or the like are also can be used. Abovementioned petroleum resin or dicyclopentadiene resin comprise an unhydrogenated, partially hydrogenated, or fully hydrogenated product of a homopolymer or a copolymer of $C_5$ fraction (including cyclopentadiene, isoprene, piperylene, 2-methylbutene-1,2-methylbutene-2 and the like) obtained by steam cracking of petroleum, or a homopolymer or a copolymer of $C_9$ fraction (including styrene, vinyl toluene, α-methylstyrene, indene, coumarone and the like), or a copolymer of the above $C_5$ fraction and $C_9$ fraction or the like. The above-described liquid organic compound may be used singly or two or more thereof may be used in combination, depending on the performance required. Examples of the above-described benzene polycarboxylic acid alkyl ester derivative include phthalic acid esters, trimellitic acid esters, and pyromellitic acid esters.

In the liquid organic compound herein, liquid mixtures of solid/liquid or liquid mixtures such as solid/liquid resin may be mixed separately in the production step for the serum- or plasma-separating composition.

The above-described liquid organic compound is preferably a mixture of at least one of a petroleum resin or a dicyclopentadiene resin and a benzene polycarboxylic acid alkyl ester when the thermoplastic elastomer described later is a styrene-based thermoplastic elastomer. In this case, the liquid organic compound and the thixotropic-property imparting component are more difficult to separate, and the homogeneity as a blend can be maintained for a further prolonged period.

Thixotropic-Property Imparting Component;

The serum- or plasma-separating composition of the present invention contains a thixotropic-property imparting component.

No particular limitation is placed on the thixotropic-property imparting component used in the present invention as long as the component is a material that can be dispersed in the liquid organic compound to thereby impart thixotropic-property. Examples of an inorganic thixotropic-property imparting component include inorganic fine powders produced by a known gas phase process (the process may be also referred to as a dry process) or a precipitation process. Examples thereof include hydrophilic or hydrophobic inorganic fine powders of silicon dioxide types or silicate types such as silica, clay minerals composed of kaolinite, or smectite.

As the above-described inorganic fine powder, suitably, a silica fine powder having a low content of alkali metal elements, alkaline earth metal elements or the like is desirably used. As to silica fine powders, examples of the hydrophilic silica include the products prepared by a gas phase process, for example, AEROSIL series such as AEROSIL 130, 200, and 300 (manufactured by NIPPON AEROSIL CO., LTD.), REOLOSIL series such as REOLOSIL QS10, QS20, and QS30 (manufactured by Tokuyama Corporation), and WACKER HDK series such as WACKER HDK S13, N20, and T30 (manufactured by Wacker Asahikasei Silicone Co., Ltd.).

As to the hydrophobic silica, they include the products prepared by a gas phase process, for example, AEROSIL series such as AEROSIL R972, R974, R805, R812, and OX50 (manufactured by NIPPON AEROSIL CO., LTD.), REOLOSIL series such as REOLOSIL MT10, DM30S, HM30S, KS20S, and PM20 (manufactured by Tokuyama Corporation), and WACKER HDK series such as WACKER HDK H15, H18, and H30 (manufactured by Wacker Asahikasei Silicone Co., Ltd.). Abovementioned examples are easily available and used.

Each of the hydrophilic silica and the hydrophobic silica may be used singly, or may be used in mixture. The above-described inorganic fine powder is used not only for imparting thixotropic-property but also as a specific gravity adjuster.

Examples of an organic thixotropic-property imparting component used in the present invention include organic gelling agents such as dibenzylidene sorbitol and derivatives thereof and fatty acid amides.

Examples of easily available dibenzylidene sorbitol and derivatives thereof include GEL ALL series such as GEL ALL MD and GEL ALL D (manufactured by New Japan Chemical Co., Ltd.).

In order to further facilitate blending of the organic thixotropic-property imparting component into the liquid organic compound, an organic solvent such as dimethyl sulfoxide, N,N-dimethylformamide, and 1-methyl-2-pyrrolidone may be appropriately used as an auxiliary solvent.

These inorganic or organic thixotropic-property imparting components may be used singly or two or more of these may be appropriately used in combination.

In addition, as a thixotropic-property enhancer, various organic compound having a polar group such as polyoxyethylene-polyoxypropylene block copolymers or silicone-based surfactants or the like may be appropriately used in combination.

Furthermore, in order to increase the over time stability of thixotropic-property under high-temperature and high-humidity conditions, a trace amount of purified water may be appropriately used in combination.

Thermoplastic Elastomer;

The serum- or plasma-separating composition of the present invention contains a thermoplastic elastomer.

The thermoplastic elastomer used in the present invention is a block-copolymer comprising monomers constituting a hard segment and monomers constituting a soft segment in one molecule.

The above-described hard segment refers to a crystal segment in the case of a crystalline polymer, and refers to a stiff segment having a high glass transition point (Tg) in the case of an amorphous polymer. On the other hand, the above-described soft segment refers to a segment having a low Tg and being highly flexible.

In the thermoplastic elastomer, no particular limitation is placed on the molecular weight, the number of blocks, and the like. The thermoplastic elastomer may be any of a triblock composed of (hard-soft-hard) segments, a diblock composed of (hard-soft) segments or the like, for example, or may be a mixture thereof. The thermoplastic elastomer may be one having a linear structure or branched structure, or may a mixture thereof. The thermoplastic elastomer may be one containing double bonds hydrogenated to various degrees.

In the case of a hydrocarbon-based thermoplastic elastomer, such as styrene- and olefin-based ones, the elastomer may be one into which a small number of polar groups containing a hetero element is introduced.

Thermoplastic elastomers, which have no chemically-crosslinked point, have solubility in organic solvents as well as exhibit plasticity at high temperature. At room temperature, however, thermoplastic elastomers exhibit properties as elastomers because hard segments are crystallized to become physically-crosslinked points. In the present invention, various known thermoplastic elastomers such as styrene-based, urethane-based, ester-based, amide-based, acryl-based, or olefins-based one can be employed. In order to retain the liquid organic compound in the serum- or plasma-separating composition, a combination of soft segments having a high compatibility with the liquid organic compound and hard segments having a poor compatibility with the liquid organic compound is desirably selected. No particular limitation is placed on the molecular weight, but with an excessively small molecular weight, the elastomer may lack properties as an elastomer. In contrast, with an excessively large molecular weight, the elastomer may become difficult to dissolve in the liquid organic compound. Thus, in order to further facilitate addition of the elastomer into the liquid organic compound on production of the serum- or plasma-separating composition as well as to impart more satisfactory partition-wall formability on use of the serum- or plasma-separating composition, the molecular weight, as the weight average molecular weight, is preferably 10,000 or more and 500,000 or less, more preferably 10,000 or more and 300,000 or less.

Examples of constituents of the above-described hard segment include polystyrene, polyurethane, polyesters such as polybutylene terephthalate, and polyamides.

On the other hand, examples of constituents of the soft segment include polydienes, polydienes hydrogenated to various degrees, polyethers, polyesters, and polycarbonates.

For example, in a styrene-based thermoplastic elastomer, polystyrene segments work as hard segments, and a polydiene or a polydiene hydrogenated to various degrees works as soft segments.

Example of the styrene-based thermoplastic elastomer like this include triblock copolymer such as styrene-butadiene-styrene copolymers (SBS), styrene-isoprene-styrene copolymers (SIS), styrene-ethylene-butylene-styrene copolymers (SEES), styrene-butadiene-butylene-styrene copolymers (SBBS), and styrene-ethylene-propylene-styrene copolymers (SEPS) and modified products thereof, diblock copolymers such as styrene-butadiene copolymers (SB), styrene-isoprene copolymers (SI), styrene-ethylene-butylene copolymers (SEB), styrene-butadiene-butylene copolymers (SBB), and styrene-ethylene-propylene copolymers (SEP) and modified products thereof.

As the above-described styrene-based thermoplastic elastomer, Tuftec P1500, P1083, P5051 (styrene/butadiene/butylene/styrene), H1041, H1052, H1221 (styrene/ethylene/butylene/styrene), M1911, M1913 (modified elastomer) and the like (manufactured by Asahi Kasei Chemicals Corporation), TR2787C, TR2500P (styrene/butadiene/styrene), SIS5002C, SIS5229C (styrene/isoprene/styrene), DYNARON 8600P (styrene/ethylene/butylene/styrene) and the like (manufactured by JSR Corporation) are easily available.

As the urethane-based thermoplastic elastomer, Elastollan 1180A, S80A, C80A, ET680, ET880 (ether/isocyanate, ester/isocyanate) and the like (manufactured by BASF SE) are easily available.

As the ester-based thermoplastic elastomer, Hytrel 3046, SB654 (butylene terephthalate/ether) (manufactured by DU PONT-TORAY CO., LTD.) and the like are easily available.

As the amide-based thermoplastic elastomer, Pebax 2533, 3533 (amide/ether) (manufactured by Arkema Inc.) and the like are easily available.

As the acryl-based thermoplastic elastomer, KURARITY LA1114, LA2140e, LA2250 (methyl methacrylate/butyl acrylate) (manufactured by KURARAY CO., LTD.) and the like are easily available.

As the olefin-based thermoplastic elastomer, DYNARON 6100P, 6200P (crystalline olefin/ethylene.butylene) (manufactured by JSR Corporation) and the like are easily available.

Of these, styrene-based thermoplastic elastomers are suitable because being the most flexible to thereby have an excellent compatibility with liquid resin components and easily retain fluidity as a serum- or plasma-separating composition.

A thermoplastic elastomer and a partition wall-formable liquid organic compound may be blended by dissolution under heating. An organic solvent such as toluene, N,N-dimethylformamide, and 1-methyl-2-pyrrolidone may be used as an auxiliary solvent as required.

The thermoplastic elastomer is blended in an amount of preferably 0.5 to 50% by weight, more preferably, 1 to 20% by weight, still more preferably, 1 to 10% by weight.

When the blend concentration is excessively low, the effect of maintaining the blend homogeneity is insufficient for a serum- or plasma-separating composition. In contrast, an excessively high blend concentration is not preferable because dissolution in a liquid organic compound becomes difficult. Moreover, the viscous physical properties of the composition become excessively high, and thus large centrifugal force is required for forming a partition wall.

The serum- or plasma-separating composition of the present invention comprises a liquid organic compound, a thixotropic-property imparting component, and a thermoplastic elastomer, as described above. Accordingly, the composition is less likely to cause separation between the liquid organic compound and the thixotropic-property imparting component and can maintain a homogeneous blended state for a prolonged period.

The detailed reason why the composition can maintain a homogeneous blended state for a prolonged period is unknown, but it is assumed that a non-hydrogen-bonding-based network is formed by the thermoplastic elastomer in the liquid organic compound to thereby prevent the liquid organic compound from leaking from the hydrogen-bonding-based network.

(Production Method)

No particular limitation is placed on the method for producing the serum- or plasma-separating composition provided by the present invention. For example, after the above-described liquid organic compound and the above-described thermoplastic elastomer are dissolved under heating, an inorganic powder as a thixotropic-property imparting component may be blended and mixed in the mixture. No particular limitation is placed on the mixing process, and any known kneading process may be used, such as a planetary mixer, a roll mill, and a homogenizer.

(Blood-Test Container)

The blood-test container of the present invention contains a serum- or plasma-separating composition therein. No particular limitation is placed on the shape of this blood-test container, and any known bottomed cylindrical container having an opening at one end may be used.

No particular limitation is placed on the material of the blood-test container, and any known glass or thermoplastic resin such as polyethylene, polypropylene, polystyrene, polyacrylate, polymethacrylate, polyethylene terephthalate or the like may be used.

When serum or plasma is separated from blood by using the serum- or plasma-separating composition, according to the present invention, the serum- or plasma-separating composition is contained in the bottom or side wall of the above-described blood-test container, for example, and thereafter, blood as a specimen is collected in the container.

When centrifugation is carried out with a centrifuge, cell components in the blood are precipitated downward, and serum or plasma can be obtained as a supernatant. The serum- or plasma-separating composition is positioned in an intermediate layer between these to form a partition wall for separating them.

The blood-test container may be decompressed, depending on the mode of blood collection. The inside of the blood-test container may be sterilized, in response to requirements of existing standards such as JIS or ISO.

The blood-test container of the present invention can contain any known agent for clinical test therein, depending on the test purpose. The agent can take any known form, for example, the agent may be applied onto the internal wall in advance or may be granulated and contained inside the container.

Specifically, when plasma separation is required, an anticoagulant agent such as heparin or ethylenediaminetetraacetic acid (EDTA) or their salts of alkaline metals may be contained inside the blood-test container. Alternatively, when serum separation is required, a fine powder of silicon dioxide, silicate or the like composed of silica, diatomaceous earth, kaolinite, smectite or the like, or an enzyme such as thrombin or snake venom may be contained in the blood-test container in order to shorten the blood coagulation time.

Hereinafter, the present invention will become apparent by reference to specific examples of the invention and comparative examples. Note that the present invention is not limited to the following examples.

Examples 1 to 8 and Comparative Example 1

Materials used in Examples and Comparative Examples are as follows.
(Materials Used as Liquid Organic Compound)

TABLE 1

| | | |
|---|---|---|
| Petroleum resin | Regalite S5090 | Manufactured by Eastman Chemical Company |
| Dicyclopentadiene resin | SUKOREZ SU500 | Manufactured by Kolon Industries, Inc. |
| Dicyclopentadiene resin | SUKOREZ SU90 | Manufactured by Kolon Industries, Inc. |
| Benzene polycarboxylic acid alkyl ester derivative | MONOCIZER W700 | Manufactured by DIC Corporation |

(Materials Used as Thixotropic-Property Imparting Component)

TABLE 2

| | | |
|---|---|---|
| Inorganic fine powder | AEROSIL 200CF | Manufactured by NIPPON AEROSIL CO., LTD |
| Inorganic fine powder | AEROSIL R974 | Manufactured by NIPPON AEROSIL CO., LTD |
| Organic gelling agent | GEL ALL D | Manufactured by New Japan Chemical Co., Ltd |
| Auxiliary solvent | 1-methyl-2-pyrrolidone (NMP) | Manufactured by Wako Pure Chemical Industries, Ltd. |

(Materials Used as Thermoplastic Elastomer)

TABLE 3

| | | |
|---|---|---|
| Styrene-based thermoplastic elastomer | Tuftec P1500 (styrene/butadiene/butylene/styrene) | Manufactured by Asahi Kasei Chemicals Corporation |

Example 1

A trimellitic acid ester (manufactured by DIC Corporation, product name: MONOCIZER W700) as a benzene polycarboxylic acid alkyl ester derivative and a styrene-based thermoplastic elastomer (manufactured by Asahi Kasei Chemicals Corporation, product name: Tuftec P1500) were dissolved under heating at 160° C. Then, a petroleum resin (manufactured by Eastman Chemical Company, product name: Regalite S5090) and a dicyclopentadiene resin (manufactured by Kolon Industries, Inc., product name: SUKOREZ SU500, SU90) were added to the mixture and dissolved under heating about 160° C. to prepare a liquid organic compound. A solution of dibenzylidene sorbitol (manufactured by New Japan Chemical Co., Ltd., product name: GEL ALL D) as an organic gelling agent in 1-methyl-2-pyrrolidone (NMP, manufactured by Wako Pure Chemical Industries, Ltd.) was added to the liquid organic compound, which was cooled to 35° C. Subsequently, while the liquid organic compound was stirred in a planetary mixer, a hydrophilic silica fine powder (manufactured by NIPPON AEROSIL CO., LTD., product name: AEROSIL 200CF) and a hydrophobic silica fine powder (manufactured by NIPPON AEROSIL CO., LTD., product name: AEROSIL R974) as inorganic fine powders were dispersed into the liquid organic compound followed by addition of purified water. In this manner, the serum- or plasma-separating composition of Example 1 was obtained. The content ratios of respective components blended are as shown in Table 4 below.

Examples 2 to 8 and Comparative Example 1

Serum- or plasma-separating compositions were obtained in the same manner as in Example 1 except that the content ratios of respective components blended were changed as shown in Table 4.

TABLE 4

| | Ex. | | | | | | | | Comp. Ex. |
|---|---|---|---|---|---|---|---|---|---|
| | 1 | 2 | 3 | 4 | 5 | 6 | 7 | 8 | 1 |
| S5090 | 12.30 | 8.80 | 5.00 | 1.30 | 12.00 | 7.00 | 2.50 | 0.00 | 14.50 |
| SU500 | 11.10 | 8.30 | 5.50 | 2.70 | 11.09 | 8.80 | 2.75 | 0.00 | 18.03 |
| SU90 | 26.87 | 31.17 | 35.77 | 40.27 | 26.94 | 31.34 | 38.89 | 42.50 | 19.74 |
| P1500 | 2.00 | 4.00 | 6.00 | 8.00 | 2.00 | 4.00 | 6.00 | 7.00 | 0.00 |
| W700 | 44.84 | 44.84 | 44.84 | 44.84 | 45.09 | 45.98 | 46.98 | 47.61 | 44.84 |
| GEL ALL D | 0.06 | 0.06 | 0.06 | 0.06 | 0.06 | 0.06 | 0.06 | 0.06 | 0.06 |
| NMP | 0.26 | 0.26 | 0.26 | 0.26 | 0.26 | 0.26 | 0.26 | 0.26 | 0.26 |
| 200CF | 0.71 | 0.71 | 0.71 | 0.71 | 0.71 | 0.71 | 0.71 | 0.71 | 0.71 |
| R974 | 1.79 | 1.79 | 1.79 | 1.79 | 1.79 | 1.79 | 1.79 | 1.79 | 1.79 |
| Purified Water | 0.07 | 0.07 | 0.07 | 0.07 | 0.07 | 0.07 | 0.07 | 0.07 | 0.07 |
| total | 100.00 | 100.00 | 100.00 | 100.00 | 100.00 | 100.00 | 100.00 | 100.00 | 100.00 |

(Preparation of Blood-Test Container Containing Serum- or Plasma-Separating Composition)

To each of 20 polyethylene terephthalate test tubes having a capacity of 10 ml (diameter 16 mm×length 100 mm), about 1.2 g of the above-described serum- or plasma-separating composition was placed. For each of Examples 1 to 8 and Comparative Example 1, 20 blood-test containers were prepared.

(Evaluation Method)

1)<Evaluation of Specific Gravity and Viscosity>

The specific gravity of each serum- or plasma-separating composition at 25° C. was determined by the sink-float method.

About 0.5 g of a serum- or plasma-separating composition was collected with least kneading, and the viscosity at 25° C. (shear rate=1 sec$^{-1}$) was measured with a BROOKFIELD rotational viscometer equipped with a cone-plate type rotor.

2)<Evaluation of Phase Separation Resistance>

The 20 blood-test containers having a capacity of 10 ml prepared as above for each example were divided into two groups. The containers of one group were allowed to face obliquely downward and left to stand at about 55° C. for one day, and those of the other group were allowed to face obliquely downward and were left to stand at about 55° C. for five days. These containers heated and left to stand were checked for oozing of the liquid component from the first position of the surface level of the serum- or plasma-separating composition. For containers in which oozing was observed, the length of oozing was measured and averaged to evaluate the phase separation resistance.

Examples 1 to 8 and Comparative Example 1 were also subjected to test based on the assumption of prolonged storage in an upright state.

Twenty blood-test containers having a capacity of 10 ml prepared for each example were left to stand in an upright state at 55° C. for five days and subsequently divided into two groups. The containers of one group were allowed to face obliquely downward and left to stand at 35° C. for one day, and those of the other group were allowed to face obliquely downward and left to stand at about 35° C. for five days. These containers heated and left to stand were checked for oozing of the liquid component from the first position of the surface level of the serum- or plasma-separating composition. For containers in which oozing was observed, the length of oozing was measured and averaged to evaluate the phase separation resistance.

(Evaluation Results)

Evaluation results of Examples 1 to 8 and Comparative Example 1 are summarized in Table 5.

TABLE 5

| | | Ex. | | | | | | | | Comp. Ex. |
|---|---|---|---|---|---|---|---|---|---|---|
| | | 1 | 2 | 3 | 4 | 5 | 6 | 7 | 8 | 1 |
| Specific gravity | | 1.043 | 1.043 | 1.043 | 1.043 | 1.043 | 1.043 | 1.043 | 1.043 | 1.043 |
| Viscosity (Pa · s) | | 208 | 227 | 274 | 307 | 190 | 193 | 196 | 204 | 176 |
| Liquid component oozing (mm) | 55° C., one day after | 1 | 1 | 1 | 1 | 1 | 1 | 1 | 1 | 1 |
| | 55° C., five days after | 62 | 28 | 12 | 7 | 58 | 46 | 22 | 15 | 82 |
| Liquid component oozing at 55° C., upright, five days after (mm) | 35° C., one day after | 0 | 1 | 0 | 0 | 0 | 0 | 0 | 0 | 1 |
| | 35° C., five days after | 13 | 13 | 12 | 12 | 5 | 4 | 0 | 3 | 37 |

In Examples 1 to 8, value of oozing of the liquid component during prolonged storage is obviously smaller than that in Comparative Example 1, which proves that a phase separation phenomena has been prevented.

Examples 9 to 21 and Comparative Example 2

Examples 9 to 21 were examined in order to confirm the effect of the present invention also in thermoplastic elastomers of types different from those used in Examples 1 to 8.

The thermoplastic elastomers used in Examples 9 to 21 are shown in Table 6. The content ratios of respective components blended in the serum- or plasma-separating compositions are shown in Table 7.

TABLE 6

| Styrene-based thermoplastic elastomer | Tuftec P1083 (styrene/butadiene/butylene/styrene) | Manufactured by Asahi Kasei Chemicals Corporation |
| Styrene-based thermoplastic elastomer | Tuftec P5051 (styrene/butadiene/butylene/styrene) | Manufactured by Asahi Kasei Chemicals Corporation |
| Styrene-based thermoplastic elastomer | Tuftec H1041G (styrene/ethylene/butylene/styrene) | Manufactured by Asahi Kasei Chemicals Corporation |
| Styrene-based thermoplastic elastomer | Tuftec H1052 (styrene/ethylene/butylene/styrene) | Manufactured by Asahi Kasei Chemicals Corporation |
| Styrene-based thermoplastic elastomer | SIS5002 (styrene/isoprene/styrene) | Manufactured by JSR Corporation |

TABLE 6-continued

| | | |
|---|---|---|
| Styrene-based thermoplastic elastomer | SIS5229 (styrene/isoprene/styrene) | Manufactured by JSR Corporation |
| Styrene-based thermoplastic elastomer | TR2787C (styrene/butadiene/styrene) | Manufactured by JSR Corporation |
| Styrene-based thermoplastic elastomer | TR2500 (styrene/butadiene/styrene) | Manufactured by JSR Corporation |
| Styrene-based thermoplastic elastomer | TR2001C (styrene/butadiene/styrene) | Manufactured by JSR Corporation |
| Acryl-based thermoplastic elastomer | KURARITY LA1114 (butyl acrylate/methyl methacrylate) | Manufactured by KURARAY CO., LTD. |

TABLE 7

| | Ex. | | | | | | | | | | | | | Comp. Ex. |
|---|---|---|---|---|---|---|---|---|---|---|---|---|---|---|
| | 9 | 10 | 11 | 12 | 13 | 14 | 15 | 16 | 17 | 18 | 19 | 20 | 21 | 2 |
| S5090 | 5.61 | 6.83 | 8.08 | 13.99 | | 7.50 | 11.00 | 7.60 | 5.20 | 1.76 | 2.05 | 3.56 | 3.32 | 14.50 |
| SU500 | 8.02 | 9.09 | 9.74 | 15.98 | | 9.30 | 9.30 | 9.30 | 9.30 | 6.00 | 6.00 | 9.30 | 9.30 | 18.03 |
| SU90 | 34.64 | 32.35 | 30.45 | 18.30 | | 31.20 | 28.70 | 30.60 | 32.00 | 36.85 | 36.75 | 32.45 | 33.52 | 19.74 |
| Tuftec P1083 | | | | | | 4.00 | | | | | | | | |
| Tuftec P5051 | | | | | | | 4.00 | | | | | | | |
| Tuftec H1041G | | | | | | | | 4.00 | | | | | | |
| Tuftec H1052 | | | | | | | | | 4.00 | | | | | |
| SIS5002 | | | | | | | | | | 4.00 | | | | |
| SIS5229 | 4.00 | | | | | | | | | | 4.00 | | | |
| TR2787C | | 4.00 | | | | | | | | | | 4.00 | | |
| TR2500 | | | | | | | | | | | | | 4.00 | |
| TR2001C | | | 4.00 | | | | | | | | | | | |
| KURARITY LA1114 | | | | 4.00 | 47.70 | | | | | | | | | |
| W700 | 44.80 | 44.80 | 44.80 | 44.80 | 49.37 | 45.37 | 44.37 | 45.87 | 46.87 | 48.76 | 48.57 | 48.06 | 47.23 | 44.80 |
| GEL ALL D | 0.06 | 0.06 | 0.06 | 0.06 | 0.06 | 0.06 | 0.06 | 0.06 | 0.06 | 0.06 | 0.06 | 0.06 | 0.06 | 0.06 |
| NMP | 0.30 | 0.30 | 0.30 | 0.30 | 0.30 | | | | | | | | | 0.30 |
| 200CF | 0.71 | 0.71 | 0.71 | 0.71 | 0.71 | 0.71 | 0.71 | 0.71 | 0.71 | 0.71 | 0.71 | 0.71 | 0.71 | 0.71 |
| R974 | 1.79 | 1.79 | 1.79 | 1.79 | 1.79 | 1.79 | 1.79 | 1.79 | 1.79 | 1.79 | 1.79 | 1.79 | 1.79 | 1.79 |
| Purified Water | 0.07 | 0.07 | 0.07 | 0.07 | 0.07 | 0.07 | 0.07 | 0.07 | 0.07 | 0.07 | 0.07 | 0.07 | 0.07 | 0.07 |
| total | 100.00 | 100.00 | 100.00 | 100.00 | 100.00 | 100.00 | 100.00 | 100.00 | 100.00 | 100.00 | 100.00 | 100.00 | 100.00 | 100.00 |

Examples 9 to 13 and Comparative Example 2

Serum- or plasma-separating compositions were obtained in the same manner as in Example 1 except that thermoplastic elastomers of different types were used and that the content ratios of respective components blended were changed as shown in Table 7.

Examples 14 to 21

Serum- or plasma-separating compositions were obtained in the same manner as in Example 1 except that thermoplastic elastomers of different types were used, that the auxiliary solvent, 1-methyl-2-pyrrolidone (NMP), was not used, and that the content ratios of respective components blended were changed as shown in Table 7.

(Preparation of Blood-Test Container Containing Serum- or Plasma-Separating Composition)

Twenty blood-test containers were prepared each for Examples 9 to 21 and Comparative Example 2 in the same manner as in Example 1.

(Evaluation Method)

1)<Evaluation of Specific Gravity and Viscosity>

Evaluation was carried out on Examples 9 to 21 and Comparative Example 2 in the same manner as in Example 1.

2)<Evaluation of Phase Separation Resistance>

With respect to Examples 9 to 21 and Comparative Example 2, 20 blood-test containers having a capacity of 10 ml prepared was left to stand in an upright state at about 55° C. for five days and subsequently divided into two groups. The containers of one group were allowed to face obliquely downward and left to stand at about 35° C. for one day, and those of the other group were allowed to face obliquely downward and left to stand at about 35° C. for five days. These containers heated and left to stand were checked for oozing of the liquid component from the first position of the surface level of the serum- or plasma-separating composition. For containers in which oozing was observed, the length of oozing was measured and averaged to evaluate the phase separation resistance.

(Evaluation Results)

Evaluation results of Examples 9 to 21 and Comparative Example 2 are summarized in Table 8.

TABLE 8

| | | Ex. | | | | | | | Ex. | | | | | | Comp. Ex. |
|---|---|---|---|---|---|---|---|---|---|---|---|---|---|---|---|
| | | 9 | 10 | 11 | 12 | 13 | 14 | 15 | 16 | 17 | 18 | 19 | 20 | 21 | 2 |
| Specific gravity | | 1.045 | 1.045 | 1.045 | 1.045 | 1.045 | 1.045 | 1.045 | 1.045 | 1.045 | 1.045 | 1.045 | 1.045 | 1.045 | 1.045 |
| Viscosity (Pa · s) | | 283 | 265 | 270 | 134 | 200 | 178 | 176 | 183 | 191 | 196 | 187 | 182 | 181 | 183 |
| Liquid component oozing at 55° C., upright, five days after (mm) | 35° C., one day after | 0 | 0 | 1 | 1 | 1 | 0 | 1 | 0 | 0 | 0 | 0 | 1 | 1 | 5 |
| | 35° C., five days after | 8 | 5 | 11 | 20 | 22 | 2 | 14 | 3 | 1 | 2 | 0 | 3 | 2 | 44 |

In Examples 9 to 21, value of oozing of the liquid component during prolonged storage is obviously smaller than that in Comparative Example 2, which proves that a phase separation phenomena has been prevented.

From the above, it has been found that the serum- or plasma-separating compositions of Examples 1 to 21, in which a thermoplastic elastomer is blended, can maintain the homogeneity of the blended state of components for a prolonged period against the aggregative separation force caused by a hydrogen-bonding-based network of an inorganic fine powder, an organic gelling agent, or the like.

The invention claimed is:

1. A serum- or plasma-separating composition comprising a liquid organic compound, a thixotropic-property imparting component, and a thermoplastic elastomer, wherein the liquid organic compound comprises a liquid resin.

2. The serum- or plasma-separating composition according to claim 1, wherein the thermoplastic elastomer is at least one selected from the group consisting of styrene-based thermoplastic elastomers, urethane-based thermoplastic elastomers, ester-based thermoplastic elastomers, amide-based thermoplastic elastomers, acryl-based thermoplastic elastomers, and olefin-based thermoplastic elastomers.

3. The serum- or plasma-separating composition according to claim 1, wherein the thermoplastic elastomer is a styrene-based thermoplastic elastomer.

4. The serum- or plasma-separating composition according to claim 1, wherein the content of the thermoplastic elastomer is 0.5 to 50% by weight.

5. The serum- or plasma-separating composition according to claim 1, wherein the liquid resin component is a mixture of at least one of a petroleum resin and a dicyclopentadiene resin with a benzene polycarboxylic acid alkyl ester.

6. The serum- or plasma-separating composition according to claim 1, comprising an inorganic fine powder as the thixotropic-property imparting component.

7. The serum- or plasma-separating composition according to claim 6, wherein the inorganic fine powder is at least one of hydrophilic silica and hydrophobic silica.

8. The serum- or plasma-separating composition according to claim 1, further comprising an organic gelling agent.

9. A blood-test container containing the serum- or plasma-separating composition according to claim 1 therein.

10. A method of stabilizing a serum- or plasma-separating composition, wherein a serum- or plasma-separating composition comprising a liquid organic compound and a thixotropic-property imparting component is allowed to additionally contain a thermoplastic elastomer, wherein the liquid organic compound comprises a liquid resin.

* * * * *